United States Patent
Wen et al.

(10) Patent No.: US 9,011,506 B2
(45) Date of Patent: Apr. 21, 2015

(54) BONE SCREW

(75) Inventors: Xiaoyi Wen, Shanghai (CN); Jie Li, Shanghai (CN); Zhenjie Lv, Shanghai (CN); Daozhi Liu, Shanghai (CN)

(73) Assignee: Shanghai Microport Orthopedics Co., Ltd., Shanghai (CN)

( * ) Notice: Subject to any disclaimer, the term of this patent is extended or adjusted under 35 U.S.C. 154(b) by 75 days.

(21) Appl. No.: 13/510,726

(22) PCT Filed: Nov. 5, 2010

(86) PCT No.: PCT/CN2010/078457
§ 371 (c)(1),
(2), (4) Date: May 18, 2012

(87) PCT Pub. No.: WO2011/060690
PCT Pub. Date: May 26, 2011

(65) Prior Publication Data
US 2012/0232600 A1    Sep. 13, 2012

(30) Foreign Application Priority Data

Nov. 20, 2009  (CN) .......................... 2009 1 0199188

(51) Int. Cl.
*A61B 17/86*    (2006.01)

(52) U.S. Cl.
CPC ........... *A61B 17/863* (2013.01); *A61B 17/8625* (2013.01)

(58) Field of Classification Search
USPC ........... 606/300–321; 411/307–311, 412, 413
See application file for complete search history.

(56) References Cited

U.S. PATENT DOCUMENTS

| | | | | |
|---|---|---|---|---|
| 2,788,046 A * | 4/1957 | Rosan | ........................ | 411/311 |
| 3,683,437 A * | 8/1972 | Larson | ........................ | 470/10 |
| RE27,678 E * | 6/1973 | Orlomoski | ................... | 411/311 |
| 3,850,215 A * | 11/1974 | Orlomoski | ................... | 411/311 |
| 3,882,917 A * | 5/1975 | Orlomoski | ................... | 411/309 |
| 4,103,422 A * | 8/1978 | Weiss et al. | ................... | 433/215 |
| 4,764,067 A * | 8/1988 | Kawashima | .................. | 411/310 |
| 5,957,646 A * | 9/1999 | Giannuzzi et al. | ........... | 411/412 |
| 6,129,730 A * | 10/2000 | Bono et al. | .................... | 606/291 |
| 6,216,510 B1 | 4/2001 | Hashimoto | | |
| 6,371,709 B1 * | 4/2002 | Papafotiou et al. | .......... | 411/412 |
| 6,514,025 B2 | 2/2003 | Watanabe | | |
| 6,860,690 B2 * | 3/2005 | Watanabe | .................... | 411/411 |

(Continued)

FOREIGN PATENT DOCUMENTS

WO    99/24191    5/1999

OTHER PUBLICATIONS

PCT/CN2010/078457 International Search Report dated Jan. 27, 2011 (Translation, 5 pages).

*Primary Examiner* — Christian Sevilla
*Assistant Examiner* — Eric S Gibson
(74) *Attorney, Agent, or Firm* — Michael Best & Friedrich LLP

(57) ABSTRACT

A bone screw comprises a threaded portion. The threaded portion has a first thread including a first front surface (11), a first back surface (12) and a crest. A second thread including a second front surface (16) and a second back surface (17) is formed on at least part of the crest of the first thread. Because of the presence of the second thread, a contact area between the screw and a bone and an axial pullout force-bearing area are both significantly increased, without significantly influencing the bending resistance, so that the mechanical property of the screw is entirely improved.

18 Claims, 11 Drawing Sheets

(56) References Cited

U.S. PATENT DOCUMENTS

| | | | |
|---|---|---|---|
| 6,976,818 B2* | 12/2005 | Levey et al. | 411/412 |
| 7,458,759 B2* | 12/2008 | LeVey | 411/412 |
| 7,935,138 B1* | 5/2011 | Richelsoph | 606/313 |
| 8,075,604 B2 | 12/2011 | Denis et al. | |
| 8,221,119 B1* | 7/2012 | Valen | 433/174 |
| 2005/0191150 A1* | 9/2005 | Bickford | 411/307 |
| 2005/0228388 A1 | 10/2005 | Brodke et al. | |
| 2008/0288002 A1* | 11/2008 | Crall et al. | 606/308 |
| 2009/0018591 A1* | 1/2009 | Hawkes et al. | 606/301 |
| 2009/0171401 A1* | 7/2009 | Zehnder et al. | 606/301 |
| 2009/0248087 A1* | 10/2009 | Lewis et al. | 606/301 |
| 2012/0232600 A1* | 9/2012 | Wen et al. | 606/315 |

\* cited by examiner

BONE SCREW

CROSS-REFERENCE TO RELATED APPLICATIONS

This application is a national stage filing under 35 U.S.C. 371 of International Application No. PCT/CN2010/078457, filed Nov. 5, 2010, which claims priority benefits to Chinese Patent Application No. 200910199188.6, filed Nov. 20, 2009. These applications are incorporated herein by reference in their entirety.

TECHNICAL FIELD

The present invention relates to a bone screw having improved mechanical characteristics, which is applicable to the connection of broken bones and the correction of trauma and abnormalities of bones at positions such as the cervical spine, the spine, the skull, etc.

BACKGROUND ART

In an orthopedic operation, a bone screw is generally used to connect broken bones or to correct various trauma and abnormalities of bones. Since bones are the main force receiving structures by which human bodies bear various mechanical loads, and broken bones that have been connected or the bones that have been corrected are likely to transfer the force loads borne to the bone screws for fixation, thereby in actual use, the bone screw generally needs to bear various kinds of changing forces in different frequency. This not only requires that the bone screw itself should be very strong so as not to be damaged under an action of an external force, but also requires that the bone screw should be fixedly engageable with bone tissues so as not to escape from the bones under external force.

With respect to the first requirement, the main representation is that the bone screw has a comparatively high bending strength and will not break under an action of an external force perpendicular to the direction of the axis. With respect to the second requirement, the main representation is that the bone screw not only will not escape under axial pullout force, but also can hardly rotate along an axis under moment.

In order to increase the capability of resisting the axial pullout force and an axial turning moment of the bone screw, a traditional method is increasing the height of the tooth form of the threads and increasing the density of the threads. This will significantly increase the contact surface area of the bone screw and the bone to thereby significantly increase the force receiving areas of the axial pullout force and the axial turning moment, thereby improving the axial pullout force and the axial turning moment that can be borne by the bone screw. However, such a method may cause adverse effects on the other mechanical properties of the bone screw.

For example, with regard to the bending strength of the screw, the increase of the height of the tooth form of the threads may make the inner diameter of the thread decrease relatively, which makes the cross section area of the screw capable of bearing a bending stress decrease and the bending strength decrease significantly. In particular, when the density of the threads is comparatively high, a sharp bending angle is likely to be formed at the root, which results in stress concentration and further reduces the bending strength of the screw. Besides, the height of the tooth form being too high and the axial size of the tooth form being too small will result in break of a thread tooth.

On the other hand, in order to maintain a comparatively high bending strength, the inner diameter of the threads has to be increased to thereby reduce the height of the tooth form of the threads, and the result is that dense threads having a low height of the tooth form are formed on the surface of the screw. Obviously, the capacity of resisting the axial pullout force and the axial turning moment of such a screw structure will not be too high, for the contact area of the screw and the bone is too small.

Thus, people urgently need a new bone screw, which can have the improved characteristics of resisting three external forces, i.e., the axial pullout force, the axial turning moment and the bending moment, while being contacted and engaged with the bone, thereby improving the property of the bone screw entirely.

SUMMARY OF THE INVENTION

The present invention puts forward a new bone screw, characterized in that some second threads are further formed on some area of the top of the original first thread. Since the second threads are only present at the top of the first thread, they will not reduce the inner diameter of the original first thread, and will not form the weakened root of the thread either, and thus will not weaken the bending strength of the bone screw correspondingly. However, because of the presence of the second threads, the contact surface area of the screw and the bone can be significantly increased, so that the bearing areas of the axial pullout force and the axial turning moment become large, thereby ensuring the improvement of the mechanical property of the screw.

According to one aspect of the present invention, a new bone screw is put forward, which has a first thread including a first front surface, a first back surface and a crest, and a second thread structure including a second front surface and a second back surface is formed on at least part of the crest of the first thread.

The so-called "front" and "back" directions are both mentioned with respect to the screw-in and screw-out directions of the bone screw, and in the descriptions of the present invention, the screw-in direction of the screw along the direction of the axis is called "front", and the opposite screw-out direction of the screw is called "back".

Preferably, a direction line of the second front surface in a cross section passing through an axis of the screw is substantially perpendicular to the axis of the screw. In the second thread, the second front surface mainly serves the function of bearing the axial pullout force borne by the screw, and the perpendicular second front surface can achieve engagement with the bone in a good manner to thereby uniformly bear the load on the entire second front surface.

However, the second front surface is not necessarily a planar structure, and any structure of the second front surface that can effectively bear the axial pullout force, e.g., various irregular arc surfaces, can be employed. In order to clearly describe these structures, the concept "direction line" is introduced to serve as a reference parameter of the second front surface. To be specific, the "direction line" is a straight line segment that connects effective parts of a related curve, i.e., parts serving the purpose of bearing or guiding, end to end, and can be used to substantially represent the tendency direction of the curve. However, the concept "direction line" is not a standard geometric concept. From the same consideration, the concept "direction line" is also used to serves as a reference in the succeeding descriptions of the first front surface, the first back surface, the second back surface, etc.

In addition, the expression "substantially perpendicular to the axis" means that the direction line is not necessarily wholly perpendicular, and can also be angled from the perpendicular line of the axis. The presence of a proper included angle will not produce any substantive effect on the capability of resisting the axial pullout force of the screw, and this proper included angle can be either an initiatively pursued angle correction to achieve improvement of other properties of the screw, or a tolerance of an angle error in the machining, thereby significantly reducing the difficulty of machining and reducing the manufacture cost.

It is generally recognized that when an included angle between the direction line of the second front surface in the cross section passing through the axis of the screw and a screw-in direction of the screw is 55-100°, and preferably 75-95°, it is substantially unnecessary to take into account the negative effect produced by the included angle on the capability of resisting the axial pullout force of the screw. The second front surface can be intentionally set to one inclined slightly backwards to thereby form a "barbed" structure, which can further improve the property of resisting the axial pullout force to a certain extent instead.

In the cross section passing through the axis of the screw, the second thread can take on various regular or irregular cross section shapes. For example, when the second front surface intersects with the second back surface, the second thread substantially takes on the shape of a triangle; when the second front surface and the bottom of the second back surface are connected by a straight line segment and/or a curve segment, the second thread substantially takes on the shape of a quadrangle, and preferably a trapezoid; and when the slopes of the second front surface and the second back surface continuously change and are finally connected, the second thread substantially takes on the shape of a semicircle.

The term "substantially" herein means that the expressions of the "triangle", "quadrangle (trapezoid)" and "semicircle" do not totally accord with the geometric definitions, e.g., the respective edges of the triangle and quadrangle (trapezoid) are not necessarily all straight line segments, and can also include regular or irregular curve segments or folded line segments, and e.g., the curvature of the semicircle edge can be gradually changing. Besides, even if the respective edges are all straight line segments, the joints of the respective edges can also form a chamfer or an arc to remove the stress concentration.

An axial size of a top and a height of the second thread are in a functional relationship with the root strengths of the front and back remaining portions of the first thread apart from the second thread. When the axial size of the top and the height are determined, the root strengths of the front and back remaining portions of the first thread should be ensured to be within a safe range, and a contact area of the second thread and the bone should be made to be as large as possible.

As stated in the part of Background Art, the capacity of resisting the axial turning moment is closely associated with the total contact area of the screw and the bone, i.e., the larger the contact area is, the larger the capacity of resisting the axial turning moment is, and the more difficult the screw-out of the screw from the bone is.

However, since the actual contact surface between the bone screw and the bone has a certain spatial geometric shape, it is very difficult to obtain an accurate value. Thus, under the circumstance where the results are not required to be very accurate, it is also permissible to use the perimeter of the second thread on the axial cross section as the basis for judging the capability of resisting the axial turning moment of the screw.

Generally speaking, the increases of the axial size of the top and the height of the second thread both can effectively improve the property of the screw. In order to obtain an obvious improvement of the property of the screw, the height of the second thread cannot be smaller than 10% of the height of a tooth form of the first thread, but in order to ensure safety, the axial size of the top cannot exceed 70% of a width of the crest of the first thread.

Preferably, a direction line of the second back surface in a cross section passing through the axis of the screw is substantially parallel to a direction line of a corresponding part of the first front surface. Such a structure can reduce the resistance borne by the screw in the screw-in process as far as possible.

The corresponding part of the first front surface refers to a part of the first front surface having the same height as the second back surface. The expression "substantially parallel" means that the two direction lines are not necessarily wholly parallel, and can also form a small included angle with each other. The presence of this small included angle will not obviously increase the resistance borne by the screw in the screw-in process, and similarly, this small included angle can be either an initiative angle correction or a tolerance of an angle error in the machining Preferably, the included angle between the two direction lines does not exceed 15°, and can be positive or negative.

With regard to a standard bone screw, the angle between the direction line of the second back surface in the cross section passing through the axis of the screw and the screw-in direction of the screw is about 105-165°, and preferably 110-135°.

Preferably, the second thread can be continuous or include a plurality of thread segments. Besides, when the second thread includes a plurality of thread segments, these thread segments may have cross section shapes that are not totally the same in the cross section passing through the axis of the screw. On the other hand, the second thread can have a changing, e.g., continuously gradually changing or abruptly changing, cross section shape in the cross section passing through the axis of the screw.

Besides, the second thread can be distributed at a front portion or any other portion of the threaded portion, and can be distributed on an entire length of the threaded portion. The second thread can also have a changing thread pitch.

The above solutions are all optional optimizations and adjustments of the second thread structure, and can further improve the property of the bone screw with respect to the specific application environment. For example, to be specific, the bones at different positions of the human body per se have different bone densities, bone developments and aging degrees of patients at various age levels are respectively different, and even with respect to the same bone, the bone density distributions from outside to inside are also different. Thus, a monotonous bone screw thread cannot be adapted to all patients and positions. Thus, in design, the screw can be made to more effectively achieve the engagement with the bone by adjusting the distribution and cross section change of the second thread according to the specific conditions of the patients.

Preferably, respective links of the second thread can be set to ones positioned at a middle portion of corresponding links of the first thread all along. Such a structure can ensure that the front and back remaining portions of the first thread have substantially equal root strengths, which can increase the axial size of the top and the height of the second thread under most of the circumstances in addition to reducing the risk of tooth break, thereby increasing the engagement area of the screw and the bone.

Preferably, the first thread can comprise a conical thread inner diameter on part of the axial length (e.g., the middle segment) thereof or the entire axial length thereof, and the second thread can employ a conical thread inner diameter in the same manner or employ a simple cylindrical thread inner diameter. The employment of the cylindrical thread inner diameter can effectively improve the capability of resisting the axial pullout force of the screw. However, since the inner diameter is comparatively thin, the screw is likely to be broken under the action of the bending stress. The employment of the conical thread inner diameter can significantly improve the capability of resisting bending of the screw. However, the capability of resisting the axial pullout force of the screw will decrease, for at the back segment of the screw, the height of the tooth form of the thread is too small. Thus, a reasonable selection of the match of the first and second threads is also a method of improving the screw with respect to a specific bone condition. Besides, the second thread and the first thread can be also made to have bottom diameter structures of corresponding shapes, e.g., the first thread and the second thread both have bottom diameter structures having cylindrical front and back portions and conical middle portions.

Further, a third thread including a third front surface and a third back surface can be further provided at a bottom of the second thread, and direction lines of the third front surface and the third back surface are substantially parallel to the direction lines of the second back surface and the second front surface respectively. Obviously, the setting of the third thread can further increase the contact surface area of the screw and the bone, so that the bearing areas of the axial pullout force and the axial turning moment become large to thereby improve the property of the screw. Besides, it is permissible to set a plurality of third threads.

In addition, the axial size of the top and the height of the second thread can be respectively selected within the ranges of 0-1.5 mm and 0-1.5 mm, and preferably the height of the second thread can be 0.05-0.75 mm.

According to another aspect of the present invention, a new cervical screw is put forward, which includes the structure according to the first aspect of the present invention. Besides, for a suitable use in the cervical spine, the height of the tooth form of the second thread of the screw is 0.1-0.5 mm, and the axial size of the top of the second thread is 0.1-0.75 mm. Preferably, the height of the tooth form is 0.15-0.35 mm, and the axial size of the top is 0.15-0.35 mm.

According to a further aspect of the present invention, a new spinal screw used in spine surgery is put forward, which includes the structure according to the first aspect of the present invention. Besides, for a suitable use in spine, the height of the tooth form of the second thread of the screw is 0.1-1.0 mm, and the axial size of the top of the second thread is 0.1-1.0 mm. Preferably, the height of the tooth form is 0.2-0.65 mm, and the axial size of the top is 0.2-0.65 mm.

According to a still further aspect of the present invention, a new cranio-maxillofacial screw used in cranio-maxillofacial surgery is put forward, which includes the structure according to the first aspect of the present invention. In order to be suitable for use in the skull, the height of the tooth form of the second thread of the screw is 0-0.25 mm, and the axial size of the top of the second thread is 0-0.35 mm. Preferably, the height of the tooth form is 0.05-0.15 mm, and the axial size of the top is 0.1-0.2 mm.

According to a still further aspect of the present invention, a new trauma screw used in trauma surgery is put forward, which includes the structure according to the first aspect of the present invention. Besides, for a suitable use in the wound, the height of the tooth form of the second thread of the screw is 0-1.5 mm, and the axial size of the top of the second thread is 0-1.5 mm. Preferably, the height of the tooth form is 0.05-0.75 mm, and the axial size of the top is 0.05-0.75 mm.

Since the bone densities of the bones to which the cranio-maxillofacial screws used in cranio-maxillofacial surgery and parts of the trauma screws used in trauma surgery are directed are very large, the second thread can achieve the function thereof as long as they have a very small size.

In addition, with respect to the cervical screws, the spinal screws used in spine surgery, and parts of the trauma screws used in trauma surgery, the height and the axial size of the top of the second thread located at the front end of the screw can be set to ones not less than the height and the axial size of the top of the second screw located at the back end of the screw. This is adapted to the characteristics of a comparatively large change of the bone densities of these bones from outside to inside, a large bone density of an outer layer cortical bone, and a small bone density of an inner layer cancellous bone.

By means of the above structures, the capability of bearing the axial pullout force and the axial turning moment of the screw in the present embodiment is significantly improved. Besides, since a sufficient size margin is kept for the first thread in design, almost no negative effects will be produced on the capability of resisting bending of the first thread.

BRIEF DESCRIPTION OF THE DRAWINGS

Now, the descriptions of the preferred embodiments of the present invention will be given only in an exemplificative manner by referring to the Drawings, in which.

DETAILED DESCRIPTION

Figure 1:
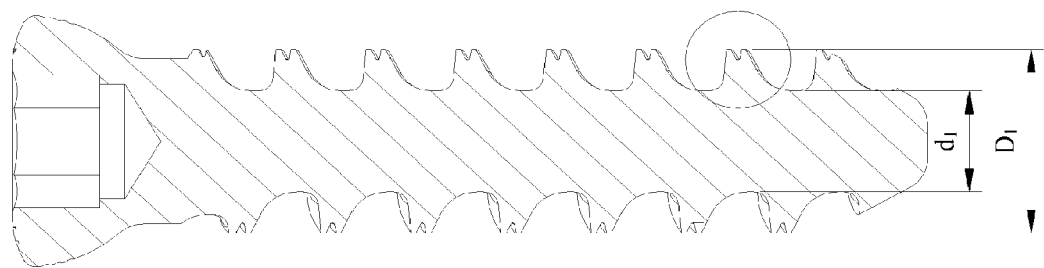
FIG. 1 shows a view of the cross section passing through an axis of the cervical screw according to a preferred embodiment of the present invention.

The detailed descriptions of the preferred embodiments of the present invention will be given in an exemplificative manner below by referring to the Drawings, so that those skilled in the art can understand the advantages of the present invention more clearly.

Figure 2:
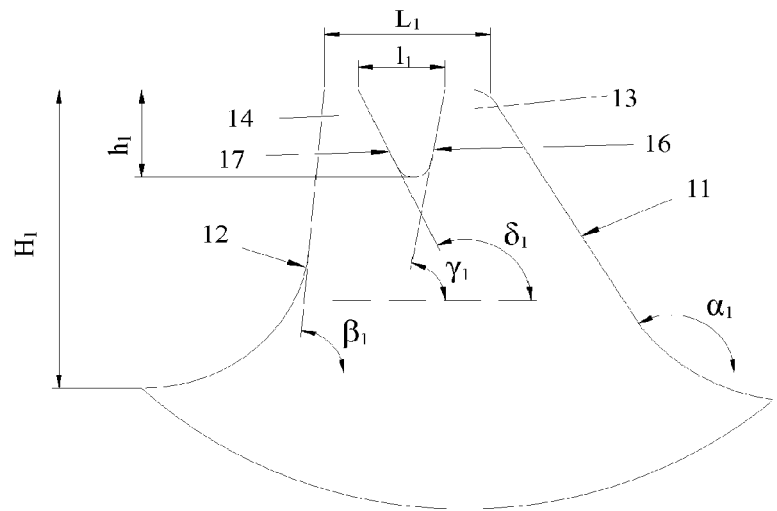
FIG. 2 shows an amplified view of the circled portion in FIG. 1, and shows a tooth form structure of the cervical screw.

First referring to FIGS. 1 and 2, they show a preferred embodiment of a cervical screw designed according to the present invention and the tooth form structure thereof. The screw is used in an anterior cervical plate system, which has been widely applied in cervical spine operations and includes fixation plates and bone screws, wherein the fixation plates and bones are fixedly connected together by the bone screws, so as to achieve connection of broken bones or correction of trauma and abnormalities of bones using the rigidity of the plate.

It can be seen from FIG. 1 that the thread inner diameter of the first thread takes on a cylindrical shape, a diameter $d_1$ is 2.2 mm, and an outer diameter $D_1$ is 4.0 mm. Correspondingly, a maximum height $H_1$ of the tooth form of the first thread is 0.9 mm.

As shown in FIG. 2, the axial cross section of the first thread employed in the present embodiment substantially takes on the shape of an oblique trapezoid, an included angle $\alpha_1$ between the front surface 11 of the axial cross section and the screw-in direction is 115°, an included angle $\beta_1$ between the back surface 12 of the axial cross section and the screw-in direction is 85°, and an axial size $L_1$ of the crest of the thread is 0.4 mm. The second thread substantially takes on the shape of an oblique triangle.

However, those skilled in the art can readily conceive that the first thread can also employ other existing thread formats, e.g., various triangular threads, square threads and trapezoidal threads of other shapes. Certainly, the first thread can employ various standard threads in the art, and such selection will not cause any effect on the application of the second thread of the present invention. In the actual use, the manufacturers will generally make a slight adjustment of the size of the first thread according to their own internal standards, and such adjustment also belongs to a known technique.

Still referring to FIG. 2, the link of the second thread is substantially positioned at the center of the top of the corresponding link of the first thread to ensure that after the formation of the second thread, the remaining portions 13, 14 of the first thread have substantially equal mechanical strengths. This can ensure more easily that the original function of the first thread is not influenced, thereby increasing the height and axial size of the second thread to a larger extent.

The front surface 16 and the back surface 17 of the second thread take on the shape of two straight line segments located at front and back sides respectively in the cross section passing through the axis of the screw, and the bottoms of the two straight line segments are connected via an arc chamfer to remove the stress concentration. A height $h_1$ of the second thread is 0.22 mm, and an axial size $l_1$ of the top is 0.2 mm, thereby a sufficient axial size of the bottom is saved for the front and back remaining portions 13, 14 of the first thread, so that the remaining portions 13, 14 have sufficient root strengths, and will not undergo accidents such as tooth break in use.

The front surface 16 of the second thread is mainly used for bearing the axial pullout force. Accordingly, it is required that the front surface 16 should have a comparatively large slope so as not to screw out from the bone in use. Generally speaking, the front surface 16 perpendicular to the axis can achieve this object, and it is also permissible to provide the front surface 16 with an included angle with the perpendicular plane, e.g., in the present embodiment, an included angle $\gamma_1$ between the front surface 16 and the screw-in direction is 80°.

The back surface 17 of the axial cross section is mainly used for introducing the screw-in of the screw. Thus, on the one hand, the slope of the back surface 17 is generally smaller than that of the front surface 16 to thereby reduce the friction moment which blocks the screw-in. On the other hand, the slope of the back surface 17 may be substantially equal to that of the front surface 11 of the first thread, to avoid the conflict between the receiving force on the back surface 17 and the receiving force on the first front surface 11 in the screw-in process which increases the resistance of the screw-in. For example, in the present embodiment, $\delta_1$ is 115°, which is equal to the included angle $\alpha_1$ between the first front surface 11 and the screw-in direction.

Certainly, those skilled in the art can readily make various improvements based on the above embodiment. For example, each of the edges of the cross section of the second thread is not necessarily formed of a single straight line segment, and can also comprise a curve segment or a combination of a straight line segment and a curve segment.

Various data values can be also selected as desired, e.g., in another embodiment (referring to FIG. 2 for the structure), an outer diameter $D_1'$ of the first thread changes into 4.5 mm, an inner diameter $d_1'$ changes into 2.8 mm, an included angle $\alpha_1'$ between the front surface 11 and the screw-in direction changes into 125°, a height $h_1'$ and an axial size $l_1'$ of the top of the second thread both change into 0.3 mm, an included angle $\gamma_1'$ between the front surface 16 and the screw-in direction changes into 75°, and an included angle $\delta_1'$ between the back surface 17 and the screw-in direction changes into 120°.

Figure 3:
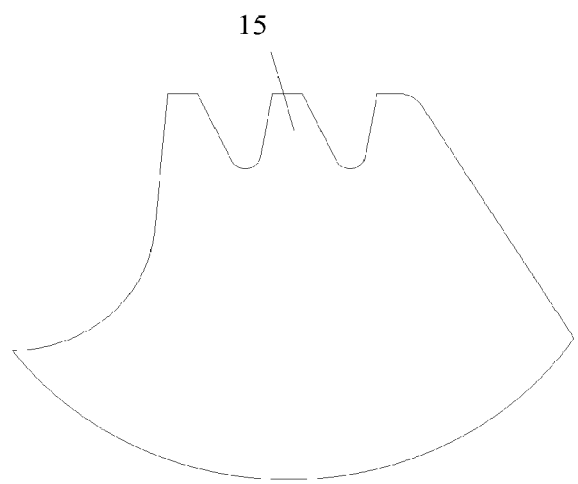
FIG. 3 shows an improved solution of the tooth form structure of the cervical screw as shown in FIG. 2.

In addition, although in the present embodiment, the top of each of the first threads is only provided with a single second thread, those skilled in the art can readily conceive that the number of the second threads can be set to several (e.g., two in FIG. 3) as desired for adaptation to the desired stress state, as long as such a structure can ensure that each of the remaining portions 13-15 of the first thread has sufficient strength and will not undergo accidents such as break. However, in a general circumstance, the employment of a single second thread can sufficiently improve the capability of bearing the axial pullout force and the axial turning moment of the screw.

Figure 4:
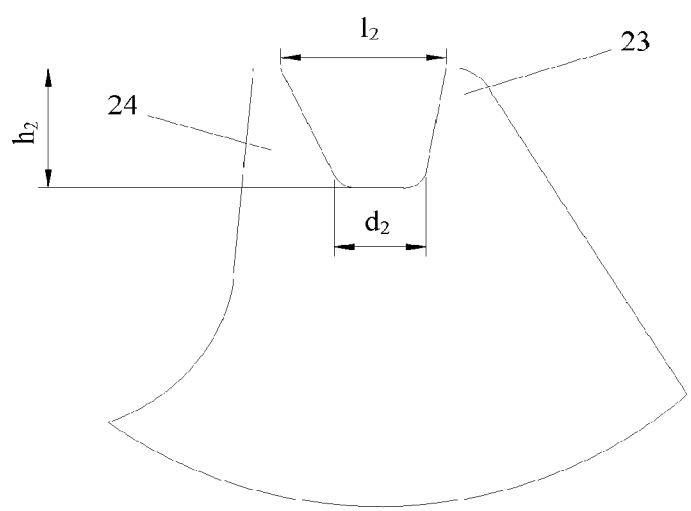
FIG. 4 shows another improved solution of the tooth form structure of the cervical screw as shown in FIG. 2.

Below, referring to FIG. 4, it shows another alternative solution of the tooth form structure of the screw shown in FIG. 2, which differs from the first embodiment in that the second thread in FIG. 4 takes on an oblique trapezoidal structure. The parameters of the first thread are not modified, and the change of the parameters of the second thread lies in that an axial size $l_2$ of the top increases to 0.25 mm, and correspondingly, radial sizes of front and back remaining portions 23, 24 of the first thread both decrease, and meanwhile $h_2$ keeps unchanged, i.e., 0.22 mm. In this case, an axial size $d_2$ of the bottom of the trapezoidal cross section changes into 0.1 mm (including sizes of chamfers on both sides).

It can be clearly found by comparing these two embodiments that in the present embodiment, since the perimeter of the cross section of the second thread further increases, the contact area of the screw and the bone correspondingly increases, thereby further improving the capability of resisting the turning moment of the screw. Meanwhile, since neither the sizes nor the angles of the front and back surfaces of the second thread change, the capability of resisting the axial pullout force of the screw is not influenced.

The only possible defect lies in that since the radial sizes of the remaining portions 23, 24 of the first thread decrease, the strengths of the remaining portions 23, 24 decrease, and the remaining portions 23, 24 may be broken at the roots in use. However, in fact, the safety and reliability of this structure can be completely ensured by reasonably setting the radial sizes of the remaining portions 23, 24.

Figure 5:
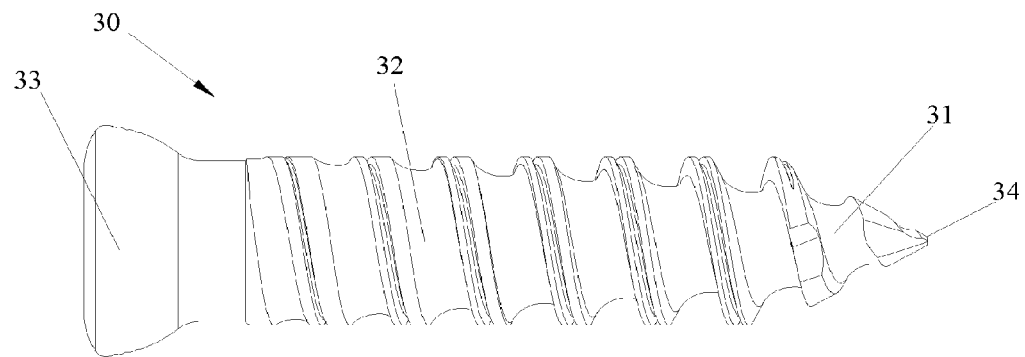
FIG. 5 shows a front view of the cervical screw according to another preferred embodiment of the present invention.
Figure 6:
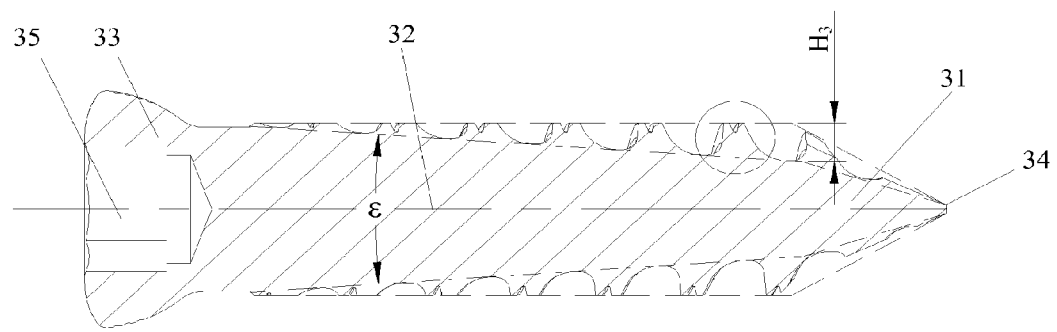
FIG. 6 shows a view of the cross section passing through an axis of the cervical screw as shown in FIG. 5.
Figure 7:
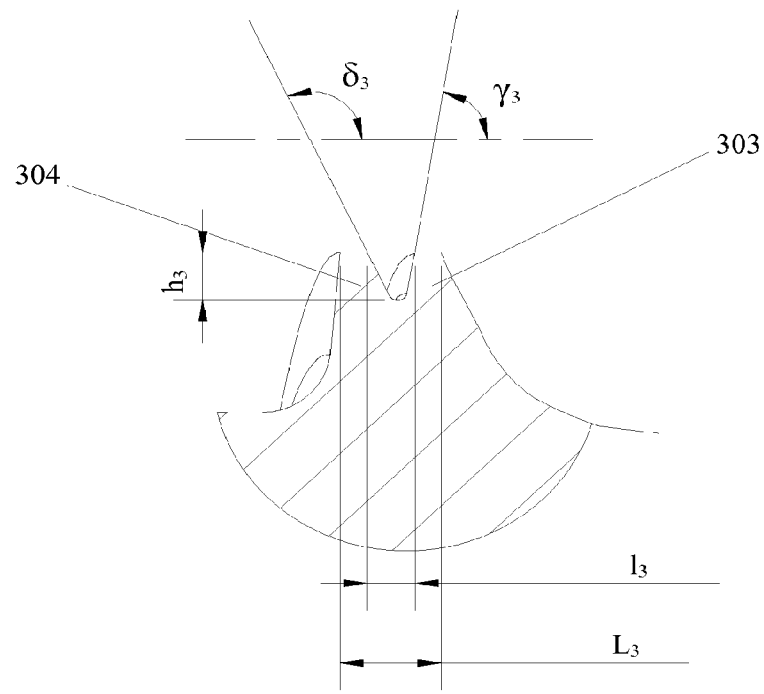
FIG. 7 shows an amplified view of the circled portion in FIG. 6, and shows a tooth form structure of the screw.

FIGS. 5-7 show another cervical screw designed according to the present invention. The structure and size of this bone screw are further improved in comparison with the previous two embodiments. FIG. 5 shows a front view of this screw, FIG. 6 splits the screw along the cross section passing through the axis in order to clearly show the thread profile of this screw, and FIG. 7 is an amplified view of a part of FIG. 6 and can show the thread shape more clearly.

In order to further optimize the stress state of the screw, the first thread in the present embodiment no longer employs a common thread structure of the inner diameter of a cylinder as the previous embodiment, but employs a bottom diameter structure of a cone with a cone angle $\epsilon$ of 3-12° which has been commonly used in the art, as shown in FIG. 6.

The bone screw 30 is made of a material commonly used in the art, e.g., biomedical titanium alloy or medical stainless steel, and has comparatively high rigidity and hardness. The bone screw 30 mainly comprises a head 31, a threaded portion 32 and a tail 33, wherein the head 31 has a tip 34, which is adapted to be nailed into the bone; the tail 33 generally has a connection portion 35 adapted to be connected with an operating member and transfer a moment, as shown in FIG. 6; and the threaded portion 32 is used to bear various changing force loads borne by the screw after the screw 30 is nailed into the bone, and the design of the shape of the threaded portion 32 has a direct effect on the mechanical property of the screw.

In the present embodiment, the structures and sizes of the head 31, the threaded portion 32 and the tail 33 employ structures and sizes of various well-known bone screws, and especially sizes of various standard screws. The manufactures will make some slight adjustments according to their internal standards, but such slight adjustments will not produce any effect on the structure and property of the screw.

Since the first thread employs a conical bottom diameter structure, as shown in FIG. 6, the parameters of the first thread continuously change on the entire length of the thread. For example, the first thread has a maximum height $H_3$ of 0.9 mm in the vicinity of the threaded portion 32 close to the head 31, and then has a height continuously decreasing as the first thread extends backwards, and finally has a height disappeared in the vicinity of the threaded portion 32 close to the tail 33.

As shown in FIG. 7, in this link of the first thread, a radial size $L_3$ of the crest of the thread is 0.42 mm, and the front surface and the back surface of this thread tooth form included angles of approximately 115° and 85° with the screw-in direction respectively, thereby forming a bearing surface of the first thread for bearing the axial pullout force and a guiding surface of the first thread for guiding the screw to be screwed in the bone respectively.

Still as shown in FIG. 7, the second thread in this embodiment is also substantially located at the center of the top of the corresponding link of the first thread as the previous two embodiments to thereby define remaining portions 303, 304 of the first thread. The second thread also substantially takes on the shape of a reversed triangle, and is formed of a front surface, a back surface and an arc connecting bottoms of the two surfaces together, wherein, an included angle $\gamma_3$ between the second front surface and the screw-in direction is 90°, and an included angle $\delta_3$ between the back surface and the screw-in direction is 125°, thereby achieving the design object of "an easy screw-in and a hard escape".

Differing from the first thread, the second thread in the present embodiment still employs a cylindrical inner diameter structure, and has a uniform size structure. The height $H_3$ of the second thread is 0.22 mm all along, and the axial size $l_3$ of the top is 0.2 mm all along. Such size selection can also effectively increase the bearing area of the axial pullout force and the contact area of the screw and the bone, thereby effectively improving the capability of resisting the axial pullout force and the turning moment without reducing the strengths of the remaining portions 303, 304 of the first thread and the bending strength of the entire screw. Certainly, the second thread can also be set to a conical bottom diameter structure the same as or different from that of the first thread by selecting proper parameters.

It should be noted that selecting proper parameters and matching the types of the first thread and the second thread not only can achieve the basic function of the present invention, but also can produce additional effects.

For example, in the present embodiment, since the first thread employs a conical bottom diameter structure, the height of the first thread continuously decreases from the maximum 0.9 mm to almost 0 from the front to the back. As a result, the contact force of the first thread and the bone is almost wholly distributed on a part of the threaded portion 32 close to the front, and especially in the vicinity of the threaded portion 32 close to the head 31, and the changing force loads are distributed in the length direction of the screw in a very non-uniform manner. The height $h_3$ of the second thread keeps unchanged, i.e., 0.22 mm, all along, which can increase the overall capability of resisting the axial pullout force and resisting the turning moment as well as especially improve the property of the back half of the threaded portion 32, thereby making the axial pullout force and the turning moment be distributed along the length of the screw in a comparatively uniform manner and additionally optimizing the overall stress state of the screw.

However, it should be understood that the stress distribution of the screw is not desired to be more uniform under all circumstances, and with respect to some specific bones, it is required that the external forces borne by these bones should be concentrated in some specific areas. A selective distribution of the external force loads can be partially achieved by selecting the types and parameters of the first thread and the second thread.

For example, with respect to the vertebral spine, due to a special change state of the bone density thereof from outside to inside, most of the loads can be only borne by the head of the screw when the screw engages with the bone. Correspondingly, to improve the overall property of the screw, the local property of this part shall be improved. Thus, the second thread which also takes on a conical bottom diameter structure, or the second thread which has the front being a cylinder and the back being a cone, or the second thread which has the front being a cone, the middle being a cylinder, and the back being a cone is more proper.

Figure 8:
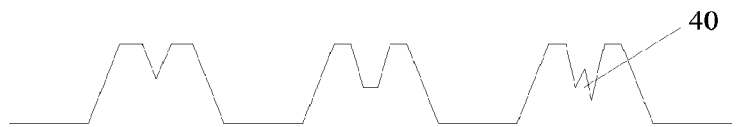
FIG. 8 shows a schematic diagram of an optional amendment solution of the second thread of the bone screw according to the present invention.

FIG. 8 shows a schematic diagram of a tooth form structure of another kind of bone screws according to the present invention. For simple descriptions, no further detailed explanations are given on the parts that have been introduced.

It can be clearly seen from FIG. 8 that the second thread herein no longer keeps the same cross section all along as the previous embodiments, but employs a setting of a changing cross section. The optional modes of changing the cross section include a gradual change, an abrupt change, and a combination of the gradual change and the abrupt change.

The advantage of the second thread employing a changing cross section lies in that the structure and parameters of the second thread can be correspondingly adjusted according to the load distribution along the length direction of the screw, thereby achieving a further optimization of the overall property of the screw.

In addition, it should be noted that FIG. 8 further shows another improved thread structure. As shown by the thread tooth at the rightmost end in FIG. 8, the bottom of the second thread can be further provided with an additional third thread 40, and as the second thread, the third thread can also improve the stress state of the screw when the screw bears various loads, thereby further improving the mechanical property of the screw.

Figure 9:
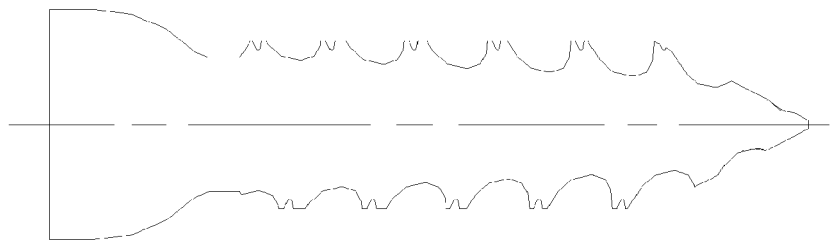
FIGS. 9a-9c show three optional distributing modes of the second thread of the bone screw according to the present invention.
Figure 9:
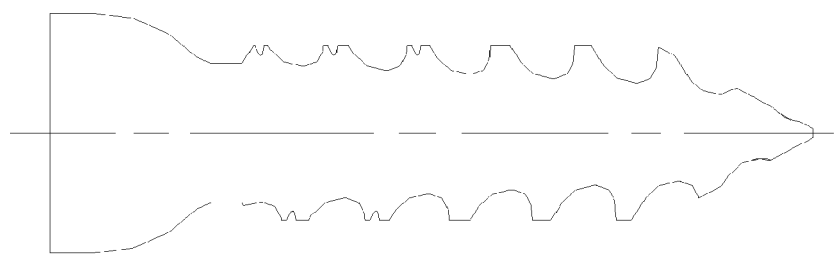
Figure 9:
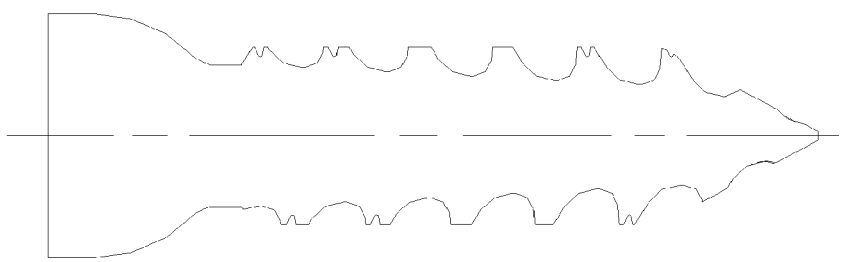

FIGS. 9a-9c show the other three optional solutions of the present invention. In FIG. 9a, the second thread is distributed at the top of the first thread along the entire axial length of the screw. The length of the second thread in this solution is the longest, and thus makes a maximum improvement of the mechanical property. However, just as described in the preceding part of the text, since the bone densities of different positions are not distributed so identically, the second thread distributed on the entire axial length are not necessary sometimes, for they are very limited in the improvement of the property and increase the machining cost in return.

Thus, sometimes people may need the second threads shown in FIGS. 9b and 9c, and these second threads are only continuously or segmentedly distributed on a part of the top of the first threads. The advantage of doing so is that the property of the screw can be optimized in a directed manner as desired. For example, the main bearing portion is reinforced, or the non-uniformity of the load distribution is improved.

Below, referring to FIGS. 10a-10d, they show four optional solutions of the bone screw when the first thread employs a conical bottom diameter structure.

FIG. 10a shows a solution of the simplest structure, i.e., setting the second thread to one having an unchanged thread pitch t all along. Such a structure is comparatively convenient in manufacturing, but may bring structural defects.

The reason lies in that since the second thread employs an arrangement mode of an equal thread pitch t, a relative position of the second thread in the top of the first thread continuously moves backwards, as shown in FIG. 10a. In this case, if the length of the screw is sufficiently long, the back surface of the second thread is excessively close to the back surface of the first thread, so that the mechanical strength of the remaining portion of the first thread close to the back is too low and the remaining portion is likely to be broken. When the length of the screw reaches a certain value, the second thread will directly cut the back surface of the first thread.

Even so, the solution in FIG. 10a is still widely applied, for this defect is not obvious under the circumstance where the length of the thread is not too large, and its machining is very convenient in the technical aspect. Besides, when the length of the thread is comparatively large, there is a need to adjust the structure and parameters of the second thread to optimize the property of the screw. FIGS. 10b-10d show such technical solutions respectively.

Figure 10:
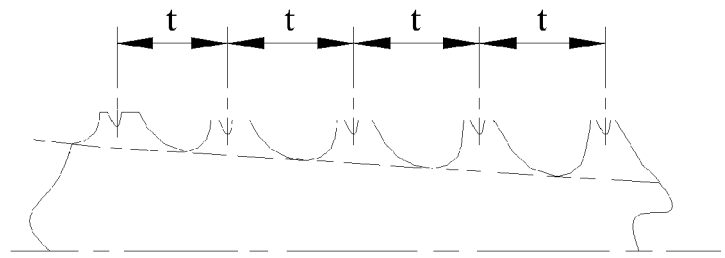
FIGS. 10a-10d show four arrangement positions of the second thread when the first thread has a conical bottom diameter structure.
Figure 10:
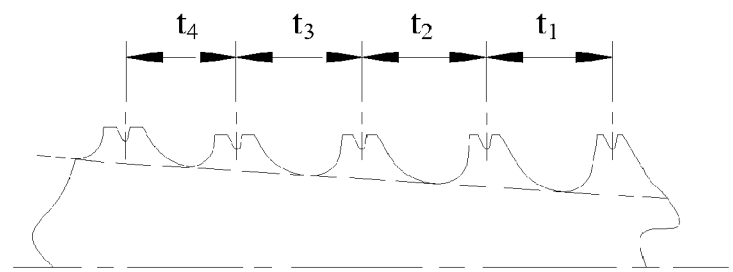
Figure 10:
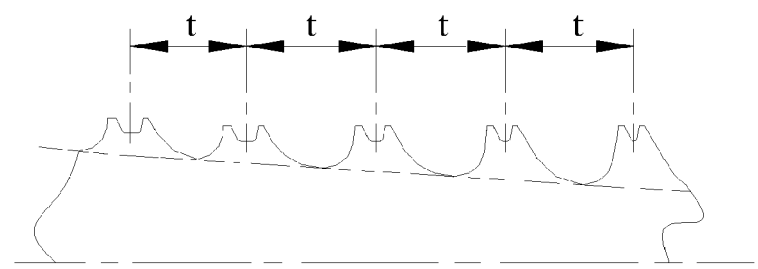
Figure 10:
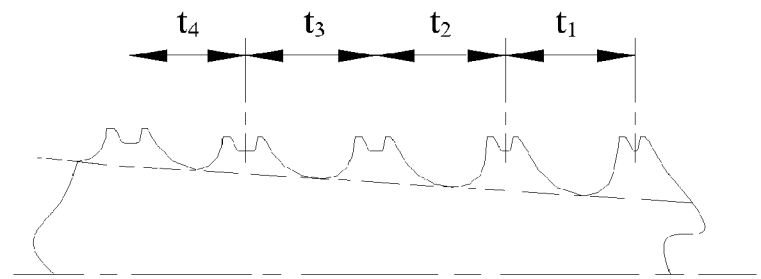
Figure 11:
FIGS. 11a-11h show several optional shapes of the second thread according to the present invention.
Figure 11:
Figure 11:
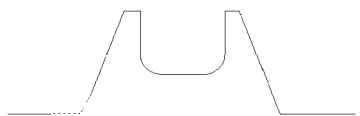
Figure 11:
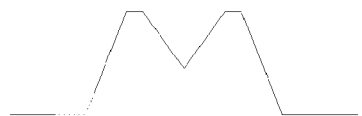
Figure 11:
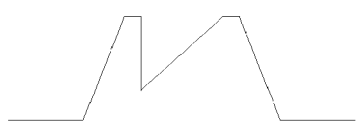
Figure 11:
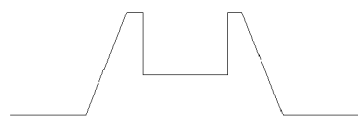
Figure 11:
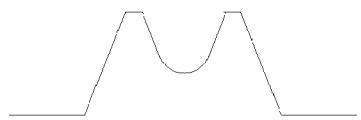
Figure 11:
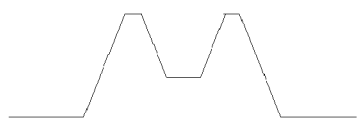

In the solution shown in FIG. 10b, the second thread is set to one with a continuously changing thread pitch (as shown by $t_1$, $t_2$, $t_3$ and $t_4$ in FIG. 10), thereby counteracting the change caused by the first thread being a conical bottom diameter structure.

In the solution shown in FIG. 10c, the second thread employs a structure with a changing cross section, which, although failing to avoid the occurrence of the above defects, can further increase the contact area of the screw and the bone instead within a safe range to thereby improve the property.

In the solution shown in FIG. 10d, the two solutions shown in FIGS. 10b and 10c are combined together to thereby improve the property and remove the risk. However, the machining process of this solution is the most complicated.

In addition, in addition to the specific structures that have been described in detail above, FIGS. 11a-11h also show several optional cross section shapes of the second thread. The second threads of these structures improve the property of the screw to different extents.

Figure 12:
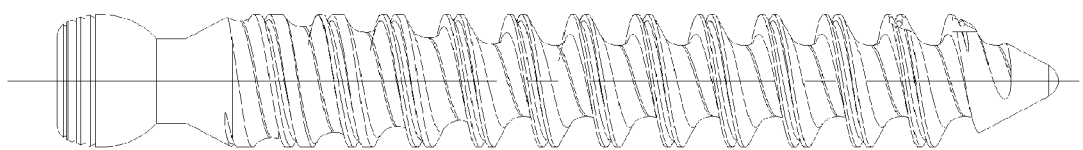
FIGS. 12-13 show a spinal screw used in spine surgery according to a preferred embodiment of the present invention.
Figure 13:
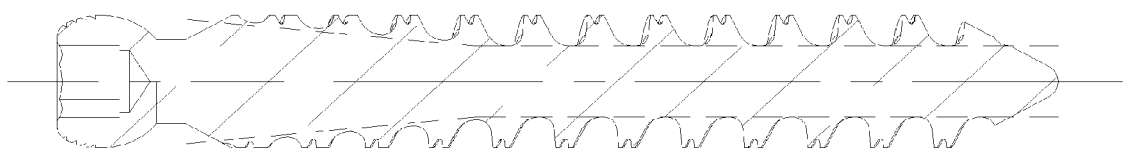

Referring to FIGS. 12-19, they show other several optional application modes of the bone screw according to the present invention, wherein:

FIGS. 12 and 13 show a spinal screw used in spine surgery according to the present invention, the front half of the first thread of the screw taking on a cylinder, and the back half of the first thread of the screw taking on a cone. The outer diameter of the first thread is 7.5 mm, the inner diameter of the first thread is 4.0 mm, the height of the tooth form in the cylinder part is of a constant value 1.75 mm, the height of the tooth form in the cone part gradually decreases, and the width of the crest is 0.84 mm. The included angles between the second back surface and the first front surface of the screw, and the screw-in direction are 115°, the included angles between the second front surface and the first back surface, and the screw-in direction are 85°, the height of the second thread is 0.35 mm, and the axial size of the top is 0.5 mm.

Figure 14:
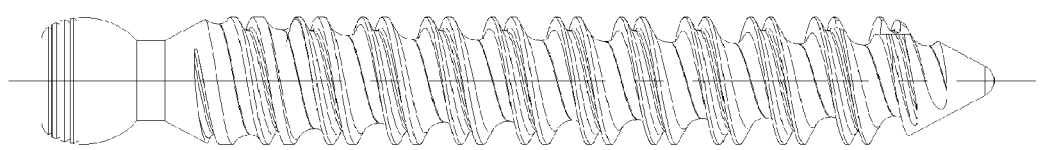
FIGS. 14-15 show another spinal screw used in spine surgery according to a preferred embodiment of the present invention.
Figure 15:
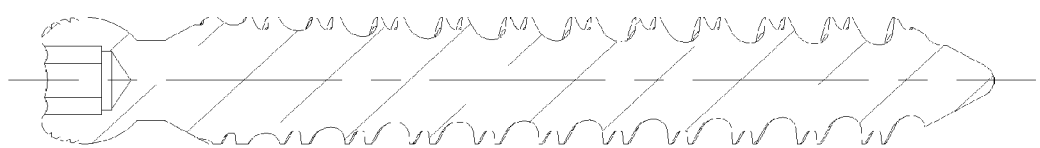

FIGS. 14 and 15 show another spinal screw used in spine surgery according to the present invention, which still has a first thread structure where the front half takes on the shape of a cylinder and the back half takes on the shape of a cone. In comparison with the previous embodiment, the difference lies in that the width of the crest of the first thread is 1.2 mm, the included angle between the second front surface and the screw-in direction is 95°, thereby the second front surface forms an included angle of 10° with the first back surface, the height of the second thread is 0.5 mm, and the axial size of the top is 0.9 mm.

Figure 16:
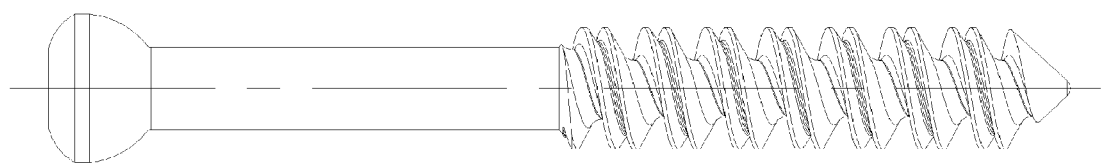
FIGS. 16-17 show a trauma screw used in trauma surgery according to a preferred embodiment of the present invention.
Figure 17:
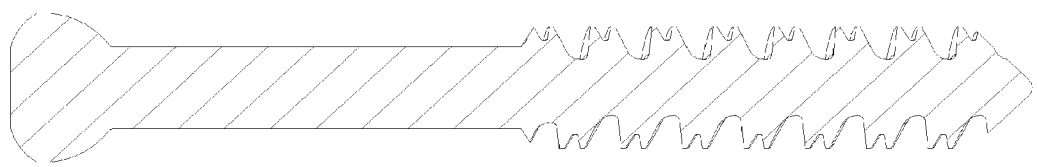

FIGS. 16 and 17 show another application of the bone screw according to the present invention, i.e., a trauma screw used in trauma surgery, the first thread of the screw being of a cylindrical shape, but being only distributed at the front half of the screw as shown in the figures, the outer diameter being 6.5 mm, the inner diameter being 3.0 mm, the height of the tooth form being 1.75 mm, and the width of the crest being 1.2 mm. The included angle between the first front surface of the thread and the screw-in direction is 115°, the included angle between the first back surface and the screw-in direction is 85°, the included angle between the second back surface and the screw-in direction is 120°, and the included angle between the second front surface and the screw-in direction is 80°, thereby forming included angles of +5° and −5° respectively. In addition, the height of the second thread is 0.75 mm, and the axial size of the top is 0.8 mm.

Figure 18:
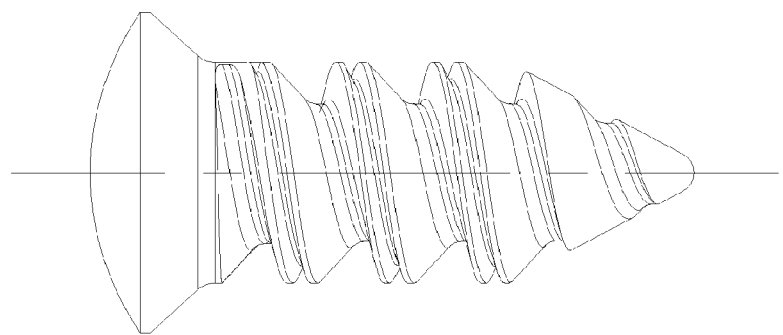
FIGS. 18-19 show a cranio-maxillofacial screw used in cranio-maxillofacial surgery according to a preferred embodiment of the present invention.
Figure 19:
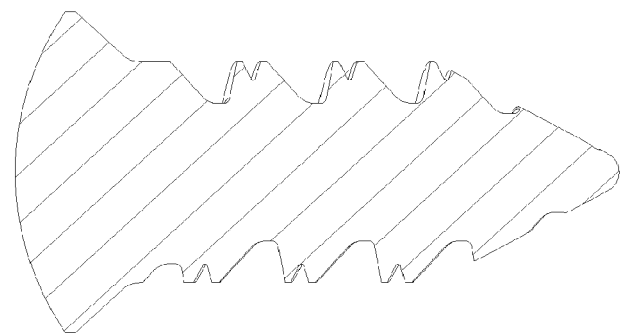

FIGS. 18 and 19 show another application of the bone screw according to the present invention, i.e., a cranio-maxillofacial screw used in cranio-maxillofacial surgery. Due to the high density of the skull, the respective size parameters of the cranio-maxillofacial screw used in cranio-maxillofacial surgery are comparatively small relative to the bone screws of other types. The outer diameter of the first thread of the cranio-maxillofacial screw used in cranio-maxillofacial surgery is 2.0 mm, the inner diameter is 1.25 mm, the height of the tooth form is 0.375 mm, and the width of the crest is 0.25 mm. The included angles between the first front surface and the second back surface of the thread, and the screw-in direction are both 130°, the included angle between the first back surface and the screw-in direction is 80°, and the included angle between the second front surface and the screw-in direction is 85°. In addition, the height of the second thread is 0.10 mm, and the axial size of the top is 0.12 mm.

Certainly, it should be understood that the contents of the present invention are not limited to the examples given in the above preferred embodiments. Those skilled in the art can readily further think of various solutions of amendments, and these optional amendments, which do not deviate from the core contents of the present invention, should also be protected as part of the present invention.

The invention claimed is:

1. A bone screw, comprising a threaded portion, which has a first thread including a first front surface, a first back surface and a crest, characterized in that a second thread including a second front surface and a second back surface is formed on at least part of the crest of the first thread, wherein the second thread includes a plurality of thread segments, and wherein the plurality of thread segments have cross sections that are not completely the same in the cross section passing through an axis of the screw, the second thread is segmentedly distributed on central portions of top ends of parts of the first thread, wherein there is no second thread on the first thread between two adjacent thread segments of the second thread, and wherein the first thread is a single thread continuously extending on the threaded portion of the bone screw.

2. The bone screw according to claim 1, characterized in that an included angle between a direction line of the second front surface in a cross section passing through the axis of the screw and a screw-in direction of the screw is 55-100°.

3. The bone screw according to claim 2, characterized in that the included angle between the direction line of the second front surface in the cross section passing through the axis of the screw and the screw-in direction of the screw is 75-95°.

4. The bone screw according to claim 1, characterized in that in a cross section passing through the axis of the screw, a cross section shape of the second thread substantially takes on a shape of a triangle or a trapezoid.

5. The bone screw according to claim 1, characterized in that an axial size of a top and a height of the second thread are in a functional relationship with root strengths of front and back remaining portions of the first thread, wherein the axial size of the top and the height are selected such that the root strengths of the front and back remaining portions of the first thread are within a safe range, and a bone contact area of the second thread is maximum.

6. The bone screw according to claim 5, characterized in that the axial size of the top of the second thread is at most 70% of a width of the crest of the first thread, and is larger than 0 mm, but smaller than or equal to 1.5 mm.

7. The bone screw according to claim 5, characterized in that a height of the second thread is at least 10% of a height of a tooth form of the first thread, and is larger than 0 mm, but smaller than or equal to 1.5 mm.

8. The bone screw according to claim 1, characterized in that an included angle between a direction line of the second back surface in a cross section passing through the axis of the screw and the screw-in direction of the screw is 105-165°.

9. The bone screw according to claim 8, characterized in that the included angle between the direction line of the second back surface in the cross section passing through the axis of the screw and the screw-in direction of the screw is 110-135°.

10. The bone screw according to claim 1, characterized in that the second thread is distributed at least one of a front portion and a back portion of the threaded portion.

11. The bone screw according to claim 1, characterized in that the second thread is distributed on an entire length of the threaded portion.

12. The bone screw according to claim 1, characterized in that a thread pitch of the second thread is changing.

13. The bone screw according to claim 1, characterized in that the second thread comprises a cylindrical thread inner diameter or a conical thread inner diameter.

14. The bone screw according to claim 13, characterized in that the cross section shape of the second thread is gradually changing or segmented, or the thread pitch of the second thread is changing, so that the second thread is located at the middle portion of the first thread all along.

15. A cervical screw, having a structure according to claim 1, characterized in that a height of a tooth form of the second thread is 0.1-0.5 mm, and an axial size of the top of the second thread is larger than 0 mm, but smaller than or equal to 0.75 mm.

16. A spinal screw used in spine surgery, having a structure according to claim 1, characterized in that a height of the second thread is 0.1-1.0 mm, and an axial size of the top of the second thread is larger than 0 mm, but smaller than or equal to 1.0 mm.

17. A cranio-maxillofacial screw used in cranio-maxillofacial surgery, having a structure according to claim 1, characterized in that a height of the second thread is 0-0.25 mm, and an axial size of the top of the second thread is larger than 0 mm, but smaller than or equal to 0.35 mm.

18. A trauma screw used in trauma surgery, having a structure according to claim 1, characterized in that a height of the second thread is 0-1.5 mm, and an axial size of the top of the second thread is larger than 0 mm, but smaller than or equal to 1.5 mm.

* * * * *